(12) United States Patent
Ebinuma (10) Patent No.: US 7,393,549 B2
(45) Date of Patent: Jul. 1, 2008

(54) DEFRUCTOSYLATION METHOD (75) Inventor: Hiroyuki Ebinuma, Ryugasaki (JP)

(73) Assignee: Daiichi Pure Chemicals Co., Ltd., Tokyo (JP)

( * ) Notice: Subject to any disclaimer, the term of this patent is extended or adjusted under 35 U.S.C. 154(b) by 193 days.

(21) Appl. No.: 10/531,321

(22) PCT Filed: Oct. 23, 2003

(86) PCT No.: PCT/JP03/13547

§ 371 (c)(1),
(2), (4) Date: Apr. 14, 2005

(87) PCT Pub. No.: WO2004/038033

PCT Pub. Date: May 6, 2004

(65) Prior Publication Data

US 2006/0240501 A1  Oct. 26, 2006

(30) Foreign Application Priority Data

Oct. 23, 2002  (JP)  ............................ 2002-308731

(51) Int. Cl.
*A01N 65/00* (2006.01)
*C12P 21/06* (2006.01)

(52) U.S. Cl. .................... 424/725; 435/68.1; 424/766

(58) Field of Classification Search ............... None
See application file for complete search history.

(56) References Cited

U.S. PATENT DOCUMENTS

| | | | | | |
|---|---|---|---|---|---|
| 4,976,974 | A | * | 12/1990 | Thumm | .......... 426/14 |
| 5,741,491 | A | * | 4/1998 | Jones | .......... 424/771 |
| 6,361,818 | B2 | * | 3/2002 | Biyani et al. | .......... 426/640 |
| 6,372,282 | B1 | * | 4/2002 | Edens et al. | .......... 426/656 |

FOREIGN PATENT DOCUMENTS

| | | | |
|---|---|---|---|
| DE | 598329 A2 | * | 5/1994 |
| EP | 1 223 224 A1 | | 7/2002 |
| JP | 60109509 | * | 6/1985 |
| JP | 5-192193 | | 8/1993 |
| JP | 6-46846 | | 2/1994 |
| JP | 7-289253 | | 11/1995 |
| JP | 8-154672 | | 6/1996 |
| JP | 8-336386 | | 12/1996 |
| JP | 11-155579 | | 6/1999 |

(Continued)

OTHER PUBLICATIONS

Mita et al., Production of fructosyl-valine for measuring hemoglobin A1c in diabetes mellitus patient, involves enzymatically treating protein whose N-terminal valine is coupled to fructose, by serine carboxypeptidase. (Physiologia Plantarum, 128 (3): 531-545, 2006).*

(Continued)

*Primary Examiner*—Patricia Leith
*Assistant Examiner*—Qiuwen Mi
(74) *Attorney, Agent, or Firm*—Oblon, Spivak, McClelland, Maier & Neustadt, P.C.

(57) ABSTRACT

The present invention is directed to a defructosylation enzyme originating from a plant, a method of defructosylating a fructosylated peptide or protein through use of the enzyme, and a method of measuring a fructosylated peptide or protein.

15 Claims, 7 Drawing Sheets

FOREIGN PATENT DOCUMENTS

| | | | |
|---|---|---|---|
| JP | 2000-333696 | | 12/2000 |
| JP | 2001-54398 | | 2/2001 |
| JP | 2001057897 | * | 3/2001 |
| JP | 2001-95598 | | 4/2001 |
| JP | 2001-095598 | | 4/2001 |
| WO | 97/13872 | | 4/1997 |
| WO | 02/06519 | | 1/2002 |
| WO | WO 02/44387 A1 | | 6/2002 |

OTHER PUBLICATIONS

Kobold, Uwe et al. "Candidate reference methods for hemoglobin A1c based on peptide mapping", Clinical Chemistry, vol. 43, No. 10, pp. 1944-1951, 1997.

Nobuyuki Yoshida, et al., "Distribution and Properties of Fructosyl Amino Acid Oxidase in Fungi", Applied and Environmental Microbiology, vol. 61, No. 12, XP-000561863, Dec. 1, 1995, pp. 4487-4489.

* cited by examiner

DEFRUCTOSYLATION METHOD

TECHNICAL FIELD

The present invention relates to a method of defructosylating a fructosylated peptide or a fructosylated protein through use of an enzyme, to a novel enzyme having defructosylating ability, and to a method of assaying a fructosylated peptide or a fructosylated protein through measuring a reaction product obtained from the defructosylation method.

BACKGROUND ART

Hemoglobin (Hb) A1c is a stable Amadori product formed through Amadori rearrangement of a Schiff base which is nonenzymatically produced between the amino group of β-chain N-terminus valine and the aldehyde group of glucose. It is also classified as a glycated protein having a structure formed of a valine residue and fructose bonded thereto. Clinically, HbA1c is correlated with a mean blood sugar level of past one to two months, and therefore, HbA1c serves as an important indicator in control of diabetes. Thus, there still exists demand for a quantitative HbA1c assay method which is rapid, convenient, accurate, and practical.

As a practical standard assay methodology for HbA1c, IFCC (International Federation of Clinical Chemistry and Laboratory Medicine) adopts a method which includes separation, by HPLC, of a β-N-terminal 6-peptide fragment which is likely to have fructosyl valine and is obtained through hydrolysis of hemoglobin with endoprotease Glu-C and quantitation of the separated fragment through capillary electrophoresis or mass spectrometry (Kobold U., et al; Candidate Reference Methods for Hemoglobin A1c Based on Peptide Mapping; Clin. Chem., 43, 1944-1951 (1997)). However, this method requires a special apparatus and entails cumbersome maneuvers and poor economy, making this method impractical.

Existing methods for measuring HbA1c which are currently employed in practice include HPLC employing, as a carrier, a special hard gel having a hydrophobic group or a cation exchange group, and latex immunoagglutination employing anti-HbA1c antibody. These existing methods, requiring expensive instruments or multi-step immunological reactions, are not necessarily satisfactory in terms of speed, convenience, or accuracy.

In recent years, there have been reported enzyme-based assay method for glycated proteins, such as HbA1c and glycated albumin, which include degradation of glycated protein with protease, and employment of fructosyl amino acid oxidase (FAOD) or a similar enzyme that reacts on a glycated amino acid (Japanese Patent Application Laid-Open (kokai) Nos. H05-192193, H07-289253, H08-154672, H06-046846, and H08-336386, WO97/13872, WO02/06519, Japanese Patent Application Laid-Open (kokai) No. 2001-054398).

In any of these methods, in order to avoid difficulty encountered by FAOD or a similar enzyme in acting on glycated protein, regardless of the glycated protein being HbA1c or glycated albumin, glycated amino acids (fructosyl valine for HbA1c; fructosyl lysine for glycated albumin) which are characteristic to respective glycated proteins are cut out from a glycated peptide or glycated protein, and the obtained glycated amino acids are used as substrates for FAOD, etc. Therefore, glycated amino acids for such purposes have to be cut out effectively so that they can serve as substrate for FAOD, etc.

To achieve the above object, research efforts have been undertaken to search for a protease which enables glycated amino acids to be effectively cut out from glycated protein, and heretofore, numerous proteases have been reported. However, no report has disclosed information about the method of cutting out the glycated amino acid (or a peptide containing the glycated amino acid) from a glycated protein, or, in more specifically, the length of the peptide chain cut out from the glycated protein. From this viewpoint, therefore, it remains unknown as to whether or not the disclosures of the above publications are in fact practical.

Meanwhile, Japanese Patent Application Laid-Open (kokai) No. 2001-95598 discloses a method for measuring glycated protein, in which a sample is treated with protease, and the resultant free-form glycated peptide is reacted with glycated peptide oxidase. In the disclosed method, however, there still remains an unsolved problem in that, since the glycated peptide oxidase substantially acts on fructosyl dipeptide, the method is not effective for a fructosyl peptide, which is longer than fructosyl dipeptide, and similar to the case of the conventional approach of using FAOD or a similar substance, a fructosyl dipeptide capable of serving as a substrate must be cut out effectively.

In another report, FAOD is used in combination with another enzyme (Japanese Patent Application Laid-Open (kokai) No. 2000-333696). However, the disclosed method is directed to improvement in measurement sensitivity by measuring hydrogen peroxide from two different sources; i.e., hydrogen peroxide generated from reaction between FAOD and glycated amino acid cut out with protease, and the other hydrogen peroxide generated from reaction between glucosone, which is a concurrently generated degradation product of glycated amino acid, and glucose oxidase. Thus, the method does not intend to perform defructosylation of glycated peptides of different lengths.

DISCLOSURE OF THE INVENTION

Accordingly, an object of the present invention is to provide an enzyme exhibiting defructosylation action on HbA1c or other fructosylated proteins, or fructosylated peptides of different sizes obtained through cutting such fructosylated proteins; a method of defructosylation by use of the enzyme; and a method of measuring fructosylated peptide or protein making use of a defructosylation reaction.

The present inventors have devoted efforts to attain the above object by searching for a useful enzyme in the natural world. As a result, they have found that, as contrasted to the fact that existing enzymes, such as FAOD, which have been reported to be endowed with defructosylation action are derived from microorganisms, certain plant families such as Rosaceae, Vitaceae, and Umbelliferae are sources of enzymes exhibiting defructosylation action, and that enzymes originating from such plants exhibit defructosylation action, regardless of the length of the peptide chain of a fructosyl peptide, thereby leading to completion of the invention.

Accordingly, the present invention provides a method for defructosylating a fructosylated peptide or protein, characterized by comprising reacting, with the peptide or protein, an enzyme which is extracted from a plant and exhibits defructosylation action.

The present invention also provides an enzyme having defructosylating a fructosylated peptide or protein, the enzyme being extracted from a plant.

The present invention also provides a method for measuring a fructosylated peptide or protein, characterized by comprising measuring at least one reaction product obtained through use of the above defructosylation method.

The defructosylation enzyme of the present invention enables defructosylation of N-terminal-valine fructosylated peptide or protein. Moreover, through quantitation of the resultant reaction product, a similar substance of N-terminal-valine fructosylated peptide, protein, or subunits of protein, e.g. HbAlc, can be quantitatively determined accurately.

BEST MODE FOR CARRYING OUT THE INVENTION

As used herein, the term "defructosylation" refers to a chemical process in which a fructosyl moiety of fructosyl amino acid or fructosyl peptide (i.e., fructosylated amino acid or fructosylated peptide) undergoes oxidation decomposition, hydrolysis, or a similar reaction, to thereby generate non-fructosylated amino acid or peptide.

No particular limitation is imposed on the enzyme employed in the present invention (hereinafter referred to as "defructosylation enzyme"), so long as the enzyme exhibits defructosylation action on a fructosylated peptide or protein. However, defructosylation enzymes originating from a plant are preferred, since such enzymes are capable of acting on fructosyl peptides having different lengths. No particular limitation is imposed on the plant containing the enzyme of the present invention. However, plants belonging to the family Rosaceae, Vitaceae, or Umbelliferae are particularly preferred. Examples of the plants belonging to the family Rosaceae include Malus, Pyrus pyrifolia, Prunus persica, and Prunus mume. Examples of the plants belonging to the family Vitaceae include Vitis vinifera and Parthenocissus tricuspidata. Examples of the plants belonging to the family Umbelliferae include Daucus carota, Oenanthe javanica, and Cryptotaenia japonica. No particular limitation is imposed on the portion of a plant employed for extracting the enzyme of the present invention, so long as the portion contains the defructosylation enzyme, and portions such as fruit, leaf, stem, flower, rhizome, and root may be employed. Alternatively, products of these plants such as juice produced from extracts and freeze-dried preparations may also be employed.

Extraction of the defructosylation enzyme from such a plant may be performed by directly disrupting and then squeezing the plant. Alternatively, prior to disruption and extraction, an appropriate buffer or a similar solution may be added to the plant. In the present invention, an extract as such may be employed. However, a purified extract is preferred. Purification may be performed through a known method. Specifically, there may be employed a suitable combination of any of ammonia sulfate fractionation processes and column chromatography processes such as ion-exchange chromatography, hydrophobic chromatography, hydroxyapatite gel, and gel filtration. In order to remove the effect of polyphenol contained in the plant extract, additional treatments may be performed through use of a reducing agent, absorbent polymer, or a similar agent.

The defructosylation enzyme of the present invention enables effective measurement of glycated protein, since the defructosylation enzyme of the present invention is capable of acting on fructosyl peptides of any size that are produced from glycated protein through protease decomposition, thus eliminating need to add another protease for cleaving the protein and time for the treatment. In addition, the defructosylation enzyme of the present invention finds utility not only in clinical tests, but also in various other fields, including the medical field. The defructosylation enzyme of the present invention may exhibit, similar to FAOD, decomposition action on the substrate fructosyl peptide through oxidation, to thereby defructosylate the peptide while generating hydrogen peroxide, glucosone, or other substances. The defructosylation enzyme of the present invention having such action is particularly preferred, since the generated hydrogen peroxide can be measured in a known measurement system through use of an enzyme such as peroxidase. Alternatively, there may be employed an enzyme which is capable of attaining defructosylation of a fructosyl peptide through hydrolysis while generating glucose, which can be measured through use of, for example, glucose oxidase.

No particular limitation is imposed on the fructosylated peptide or fructosylated protein to be treated through the defructosylation method of the present invention, so long as the defructosylation enzyme acts on the peptide or protein. However, HbAlc and fructosyl peptides having fructosylated valine at the N-terminus of a hemoglobin β-chain are particularly preferred. No particular limitation is imposed on the number of amino acid residues contained in the N-terminal-valine fructosylated peptide. However, fructosyl peptides having an amino acid sequence represented by any of SEQ ID NOs: 1 to 5 are particularly preferred.

The above-described N-terminal-valine fructosylated peptide may be prepared by treating a peptide or protein having any of the above-mentioned sequences such as HbA1c with, for example, a suitable endoprotease or exoprotease. Examples of the protease include elastase, proteinase K, pepsin, alkaline protease, trypsin, proline-specific endoprotease, V8 protease, carboxypeptidase A, and carboxypeptidase B. The protease used to prepare the fructosyl peptide preferably exhibits an activity of 0.05 to 10,000 U/mL, more preferably 10 to 2,000 U/mL.

Among a variety of conditions under which the defructosylation enzyme of the present invention is reacted with a fructosylated peptide or protein, the treatment temperature is preferably 20 to 50° C., more preferably 30 to 40° C., and the treatment time is preferably 3 minutes to 100 hours, more preferably 5 minutes to 20 hours. Through the treatment, reaction products containing glucosone or glucose and defructosyl peptides are obtained. Therefore, through measuring one or more of the reaction products, fructosylated peptide or protein can be measured.

In order to determine the enzyme activity of the defructosylation enzyme of the present invention or to determine a fructosylated peptide or protein, generated defructosyl peptides may be isolated and identified through HPLC or capillary electrophoresis. Alternatively, an appropriate carboxypeptidase may be reacted with the defructosyl peptide, to thereby detect or measure the generated amino acid residues. For example, when the fructosyl peptide having fructosylated valine at the N-terminus thereof and having an amino acid sequence represented by SEQ ID NO: 5 is reacted with carboxypeptidase, glutamic acid (Glu), proline (Pro), threonine (Thr), leucine (Leu), histidine (His), and valine (Val) are generated. Among these amino acid residues, Glu, Leu, and Val can be detected or determined by measuring the amount of NADH or NADPH produced through use of glutamate dehydrogenase, leucine dehydrogenase, and valine dehydrogenase, respectively. Glucosone or glucose produced through defructosylation can be detected or determined by generating hydrogen peroxide through use of, among other enzymes, glucose oxidase and then measuring the produced hydrogen peroxide in a peroxidase color-developing system. This process is exemplified as follows.

(Measurement of Product of Enzyme Reaction)

The enzyme of the present invention is reacted with a substrate fructosyl peptide, and the reaction mixture is heated for a predetermined period of time. To the reaction mixture (300 µL), a solution mixture which has been prepared in advance by mixing 200 mM acetate buffer (pH 6.0) (750 µL), 4,000-u/mL glucose oxidase (Toyobo Co., Ltd.) (450 µL), 0.15% 4-aminoantipyrine (300 µL), 0.3% TOOS (Dojindo Laboratories) (300 µL), 500-u/mL peroxidase (Toyobo Co., Ltd.: Type III) (300 µL), and 1% sodium azide (300 µL) is added, and the resultant mixture is treated for 10 minutes at 37° C., followed by measurement of absorbance at 550 nm. The above procedure is repeated, except that the substrate is replaced by purified water (control). The amount of the enzyme reaction product (glucosone or glucose) is calculated from the developed color through use of a calibration curve prepared by performing the same procedure in which serial dilutions of glucose are employed instead of the substrate and purified water is employed instead of the enzyme of the present invention. When a defructosylation enzyme which produces hydrogen peroxide through defructosylation reaction is employed, generated hydrogen peroxide can be directly detected or determined in a known peroxidase color-developing system.

No particular limitation is imposed on the peroxidase (POD) color-developing system. Suitable is a method in which a chromogen and POD are added to the reaction system so that the chromogen is oxidized, thereby producing a color-developing substance, followed by measuring the substance. As the chromogen, there may be employed a combination of 4-aminoantipyrine and a phenol compound, a naphthol compound, or an aniline compound, a combination of MBTH (3-methyl-2-benzothiazolinone hydrazone) and an aniline compound, leucomethylene blue, or similar substances. Alternatively, a method as described in Japanese Patent No. 2516381 may be employed. Specifically, in the presence of POD, hydrogen peroxide is reacted with divalent cobalt ion, and the produced trivalent cobalt ion is treated with a trivalent-cobalt-ion-specific indicator such as TASBB (2-(2-thiazolyazo)-5-disulfobutylaminobenzoic acid trisodium salt), thereby producing a color-developing chelate compound, followed by measuring the chelate compound. The latter method provides measurement sensitivity 5 to 10 times that provided by the former method. As an alternative reagent for detecting hydrogen peroxide, TPM-PS (N,N,N',N',N'',N''-hexa(3-sulfopropyl)-4,4',4''-triaminotriphenylmethane) (product of Dojindo Laboratories), which can be measured with high sensitivity, or a similar reagent may be employed.

According to the method of the present invention, a peptide or protein having a fructosyl valine residue at the N-terminus thereof such as HbA1c can be quantified with very high accuracy. Examples of test samples to be employed to quantify HbA1c include whole blood and erythrocyte.

EXAMPLES

The present invention will next be described in more detail by way of examples, which should not be construed as limiting the invention thereto.

Example 1

Preparation of Defructosylation Enzyme Originating from a Plant belonging to the family Rosaceae The skin and core portion including seeds of a Pyrus pyrifolia fruit were removed, and, to the remaining flesh portion, 100 mM sodium acetate (pH 4.5) (100 mL/100 g of the flesh portion) containing 300 mM sodium chloride was added, and the resultant mixture was directly crushed by means of a mixer. The product was subjected to centrifugal separation to remove solid substances, whereby a crude extract was prepared. To the crude extract, PVPP (polyvinylpolypyrrolidone: product of Nacalai Tesque, Inc.) was added in an amount of 2%, followed by stirring for 30 minutes at room temperature. Thereafter, PVPP was removed through centrifugal separation, to thereby yield a treated solution, which served as a crude enzyme solution.

Example 2

Preparation of Defructosylation Enzyme Originating from a Plant belonging to the family Vitaceae The skin of a Vitis vinifera fruit was removed, and the remaining flesh portion was crushed by means of a mixer. The product was subjected to centrifugal separation to remove solid substances, whereby a crude extract was produced, which served as a crude enzyme solution.

Example 3

Preparation of Defructosylation Enzyme Originating from a Plant belonging to the family Umbelliferae A Daucus carota rhizome was directly disrupted through use of a juicer, followed by centrifugation, to thereby remove solid substances. The thus-prepared crude extract was filtrated through use of a Millex filter (0.45 μm: product of Millipore Corporation), whereby a transparent extract was prepared. Cold ethanol (4 mL) was added to the extract (3 mL), and the formed precipitate was removed through centrifugation. To the supernatant, cold ethanol was added again, and the formed precipitate was collected through centrifugal separation. The obtained precipitate was dissolved in a small amount of 20 mM phosphate buffer (pH 7.0), to thereby prepare a crude enzyme solution.

Example 4

Method of Defructosylating Fructosyl Peptide (Use of Defructosylation Enzyme Originating from a Plant belonging to the family Rosaceae)

(i) A 100 mM acetate buffer (pH 6.0) (100 μL), a 500 μM aqueous solution (40 μL) of one of the N-terminal-valine fructosylated peptides having an amino acid sequence represented by SEQ ID NOs: 1 to 5 (f-VH to f-VHLTPE: products of Bioquest), purified water (20 μL), and the Pyrus pyrifolia-origin crude enzyme solution (40 μL) prepared in Example 1 were mixed together, and the mixture was caused to react for 64 hours at 37° C. The reaction mixture was subjected to ultrafiltration (molecular weight: 10,000), and the filtrate was collected (reaction mixtures 1 to 5, respectively). Each of the reaction mixtures 1 to 5 was analyzed through use of a capillary electrophoresis apparatus CAPI-3200 (product of Otsuka Electronics Co., Ltd.) (electrophoresis buffer: 150 mM phosphate buffer (pH 2.0), voltage: 15 kV, detection wavelength: 210 nm) in terms of peak position and peak area.

(ii) Control test

As a control, purified water was added instead of the crude enzyme solution, and the resultant mixture was allowed to react under similar conditions, to thereby prepare a filtrate (control solutions 1 to 5, respectively). The analysis results obtained from the control solutions 1 to 5 were compared with those of the reaction mixtures 1 to 5, respectively.

Each of the fructosyl peptides employed in the enzyme reaction or control test had been mixed with corresponding non-fructosylated peptide. The presence or absence of the enzyme activity was determined through comparison of the two peaks.

Figure 1:
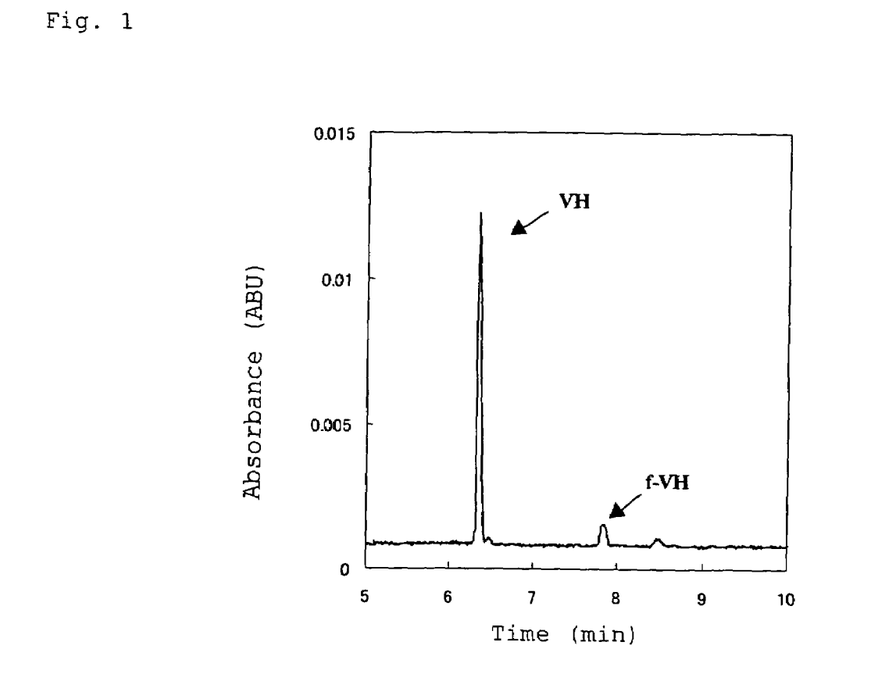
FIG. 1 shows the results of capillary electrophoresis obtained from the reaction mixture 1 prepared by reacting a Rosaceae-plant-origin defructosylation enzyme with fructosyl dipeptide (f-VH; SEQ ID NO: 1).
Figure 2:
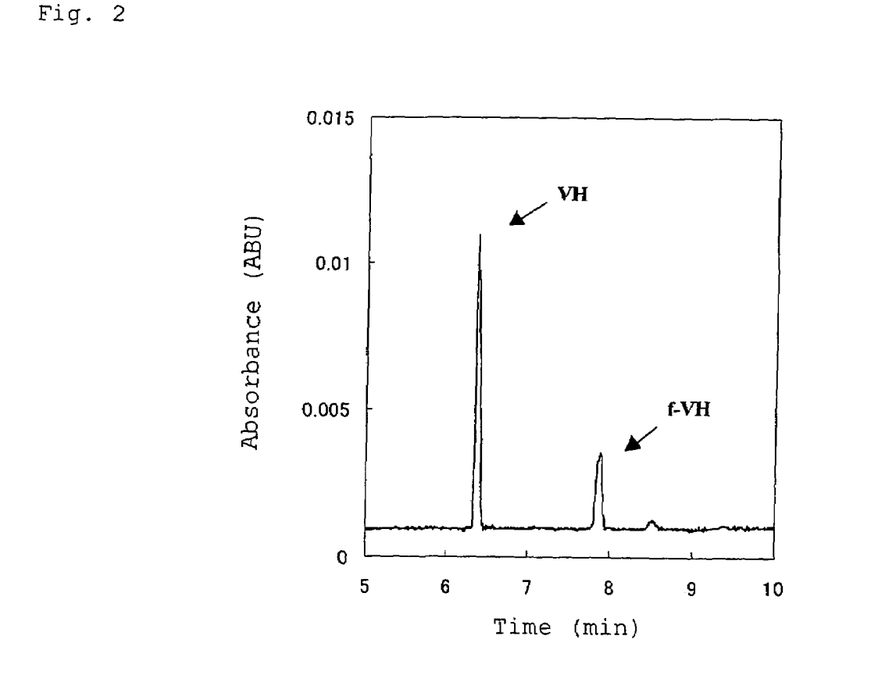
FIG. 2 shows the results of capillary electrophoresis obtained from the control solution 1 prepared by reacting purified water with fructosyl dipeptide (f-VH SEQ ID NO: 1).

FIG. 1 shows the results obtained from the reaction mixture 1, and FIG. 2 shows the results obtained from the control solution 1. Whereas FIG. 2 reveals a peak attributed to f-VH (area; 13 mABU×sec; SEQ ID NO: 1) and a peak attributed to VH (area: 34 mABU×sec; SEQ ID NO: 1), FIG. 1 reveals that the peak attributed to f-VH is lowered (area: 4 mABU×sec; SEQ ID NO: 1) and the peak attributed to VH is increased (area: 38 mABU×sec).

Figure 3:
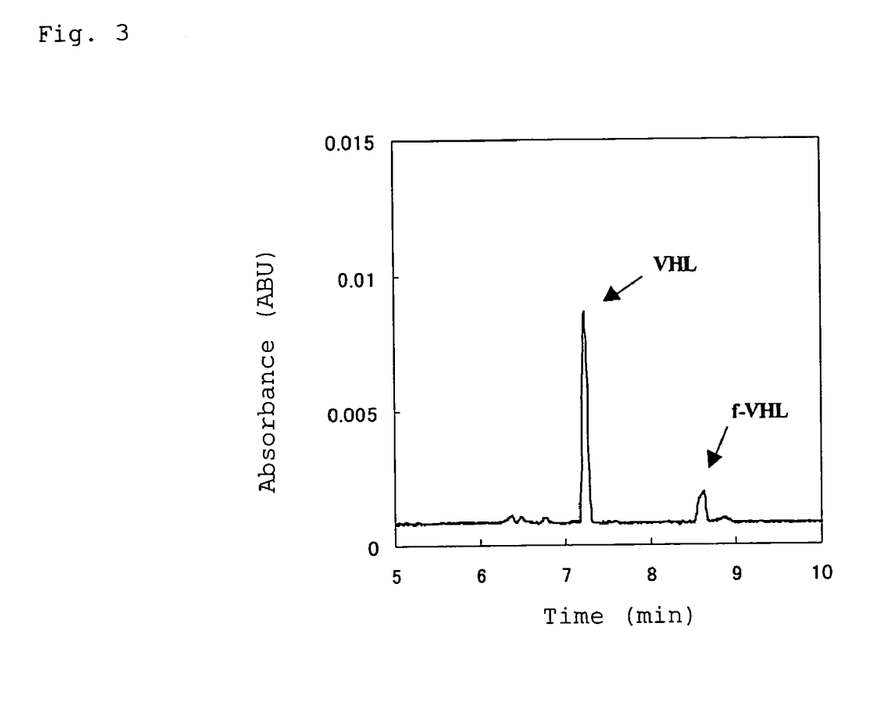
FIG. 3 shows the results of capillary electrophoresis obtained from the reaction mixture 2 prepared by reacting a Rosaceae-plant-origin defructosylation enzyme with fructosyl tripeptide (f-VHL; SEQ ID NO: 2).
Figure 4:
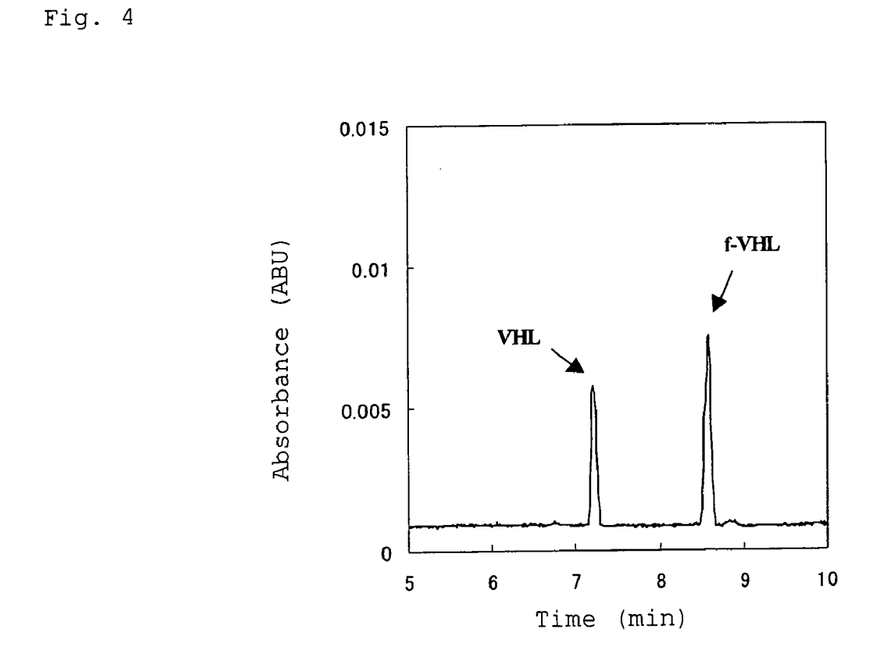
FIG. 4 shows the results of capillary electrophoresis obtained from the control solution 2 prepared by reacting purified water with fructosyl tripeptide (f-VHL; SEQ ID NO: 2).

FIG. 3 shows the results obtained from the reaction mixture 2, and FIG. 4 shows the results obtained from the control solution 2. Whereas FIG. 4 reveals a peak attributed to f-VHL (area: 32 mABU×sec; SEQ ID NO: 2) and a peak attributed to VHL (area: 22 mABU×sec; SEQ ID NO: 2), FIG. 3 reveals that the peak attributed to f-VHL is lowered (area: 7 mABU×sec; SEQ ID NO: 2) and the peak attributed to VHL is increased (area: 34 mABU×sec; SEQ ID NO: 2).

Figure 5:
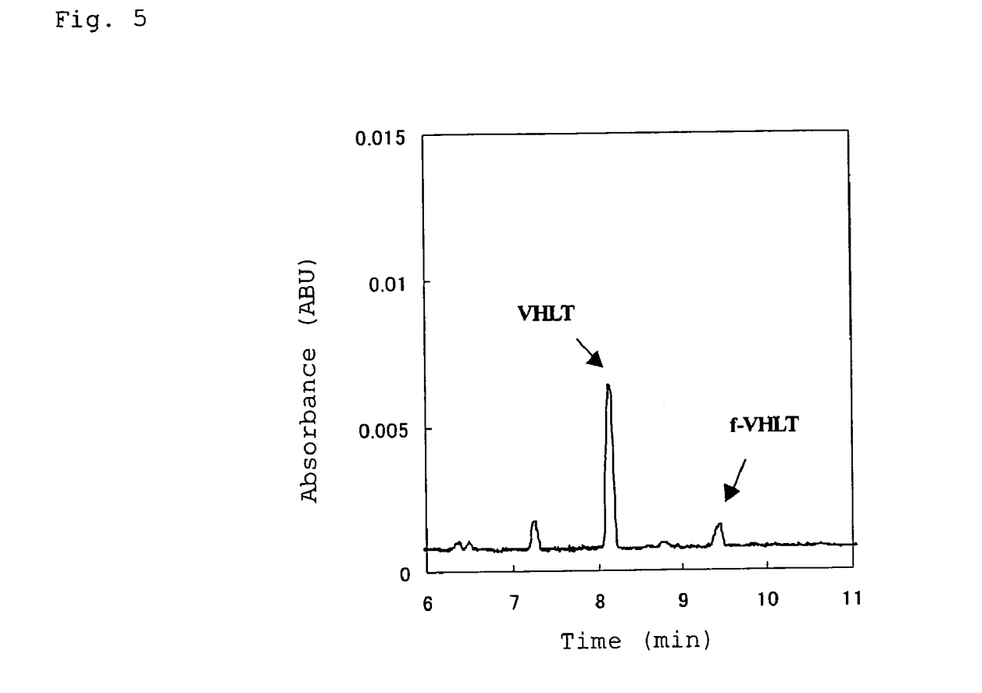
FIG. 5 shows the results of capillary electrophoresis obtained from the reaction mixture 3 prepared by reacting a Rosaceae-plant-origin defructosylation enzyme with fructosyl tetrapeptide (f-VHLTP; SEQ ID NO: 3).
Figure 6:
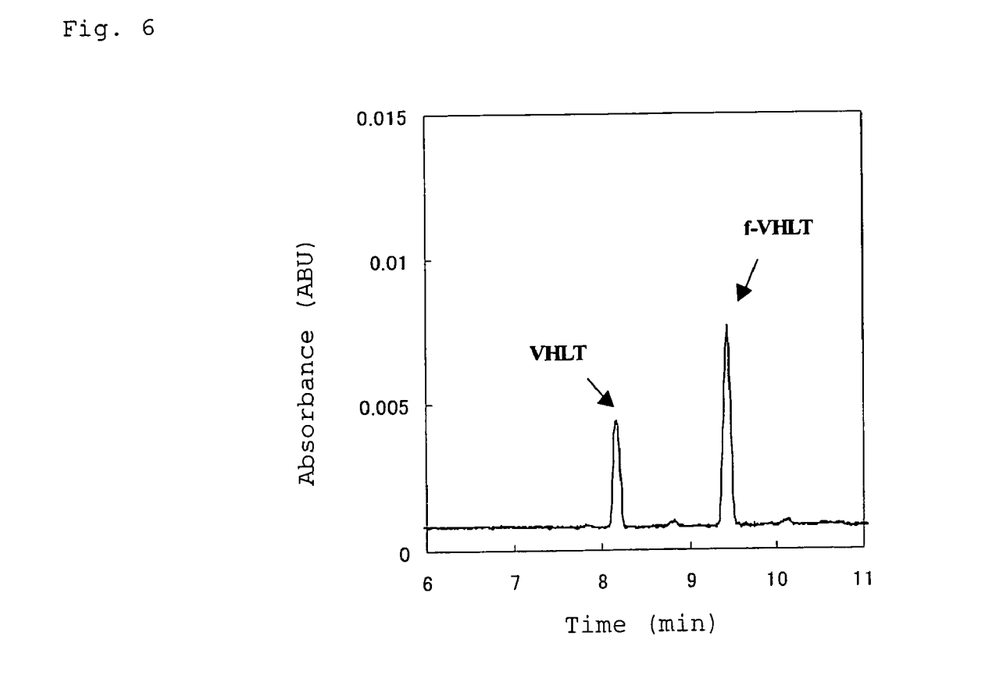
FIG. 6 shows the results of capillary electrophoresis obtained from the control solution 3 prepared by reacting purified water with fructosyl tetrapeptide (f-VHLT: SEQ ID NO: 3).

FIG. 5 shows the results obtained from the reaction mixture 3, and FIG. 6 shows the results obtained from the control solution 3. Whereas FIG. 6 reveals a peak attributed to f-VHLT (area: 38 mABU×sec; SEQ ID NO: 3) and a peak attributed to VHLT (area: 20 mABU×sec; SEQ ID NO: 3), FIG. 5 reveals that the peak attributed to f-VHLT is lowered (area: 5 mABU×sec; SEQ ID NO: 3) and the peak attributed to VHLT is increased (area: mABU×sec; SEQ ID NO: 3).

Figure 7:
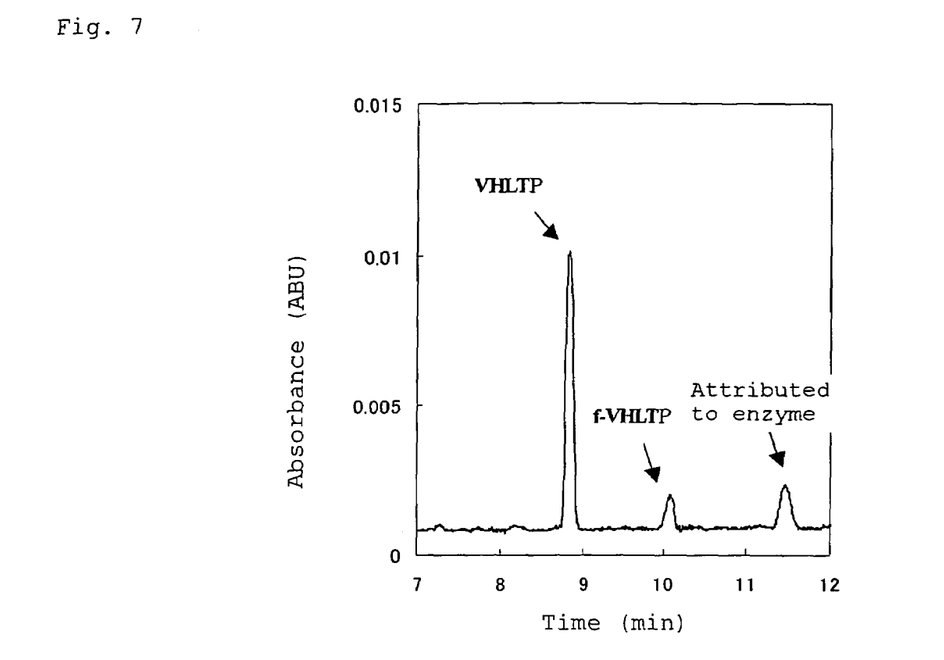
FIG. 7 shows the results of capillary electrophoresis obtained from the reaction mixture 4 prepared by reacting a Rosaceae-plant-origin defructosylation enzyme with fructosyl pentapeptide (f-VHLTP: SEQ ID NO: 4).
Figure 8:
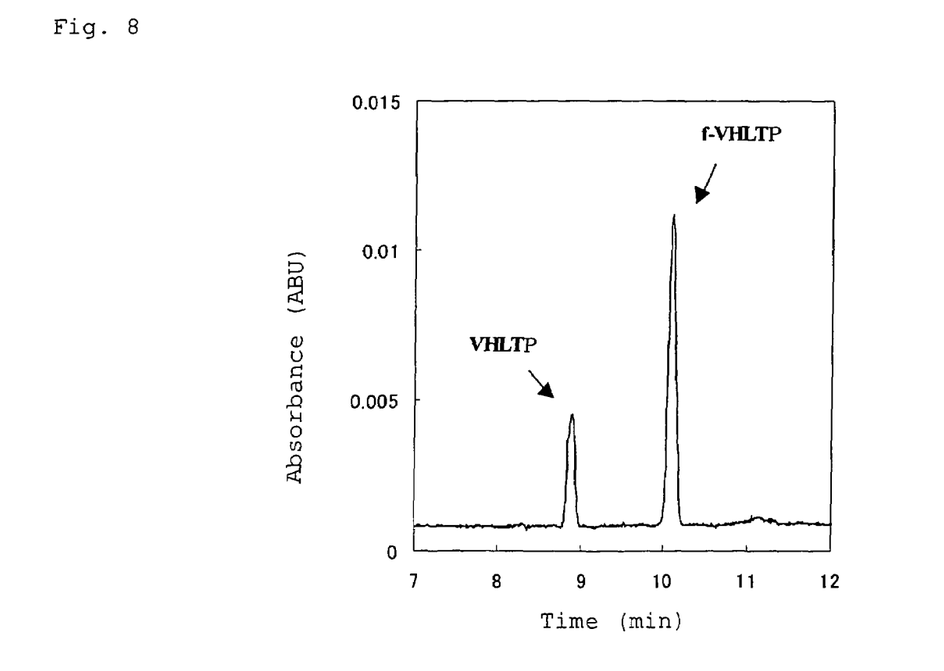
FIG. 8 shows the results of capillary electrophoresis obtained from the control solution 4 prepared by reacting purified water with fructosyl pentapeptide (f-VHLTP: SEQ ID NO: 4).

FIG. 7 shows the results obtained from the reaction mixture 4, and FIG. 8 shows the results obtained from the control solution 4. Whereas FIG. 8 reveals a peak attributed to f-VHLTP (area: 64 mABU×sec; SEQ ID NO: 4) and a peak attributed to VHLTP (area: 23 mABU×sec SEQ ID NO: 4), FIG. 7 reveals that the peak attributed to f-VHLTP is lowered (area: 8 mABU×sec; SEQ ID NO: 4) and the peak attributed to VHLTP is increased (area: 57 mABU×sec; SEQ ID NO: 4).

Figure 9:
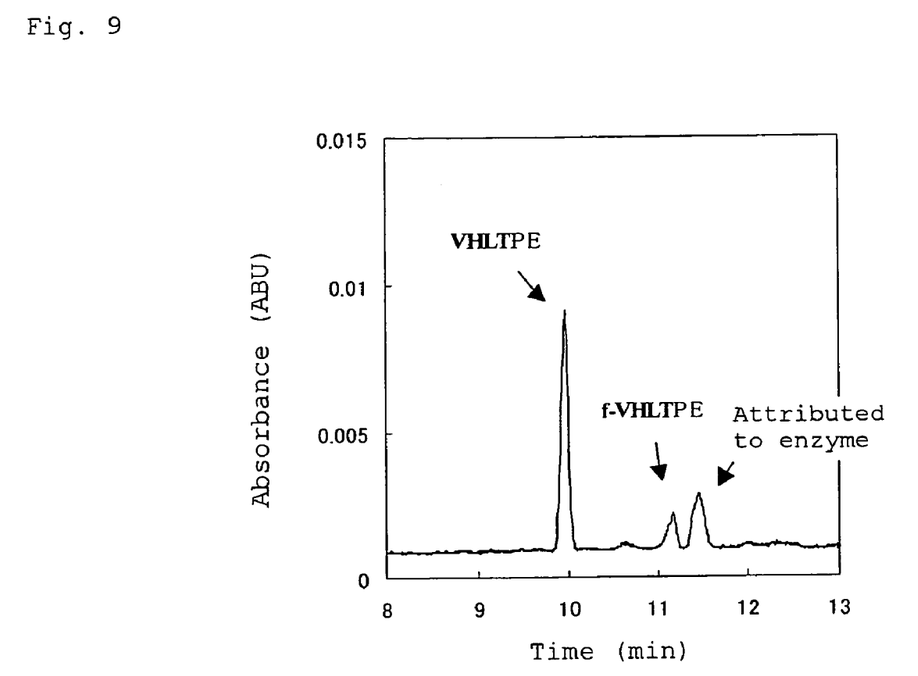
FIG. 9 shows the results of capillary electrophoresis obtained from the reaction mixture 5 prepared by reacting a Rosaceae-plant-origin defructosylation enzyme with fructosyl hexapeptide (f-VHLTPE; SEQ ID NO: 5).
Figure 10:
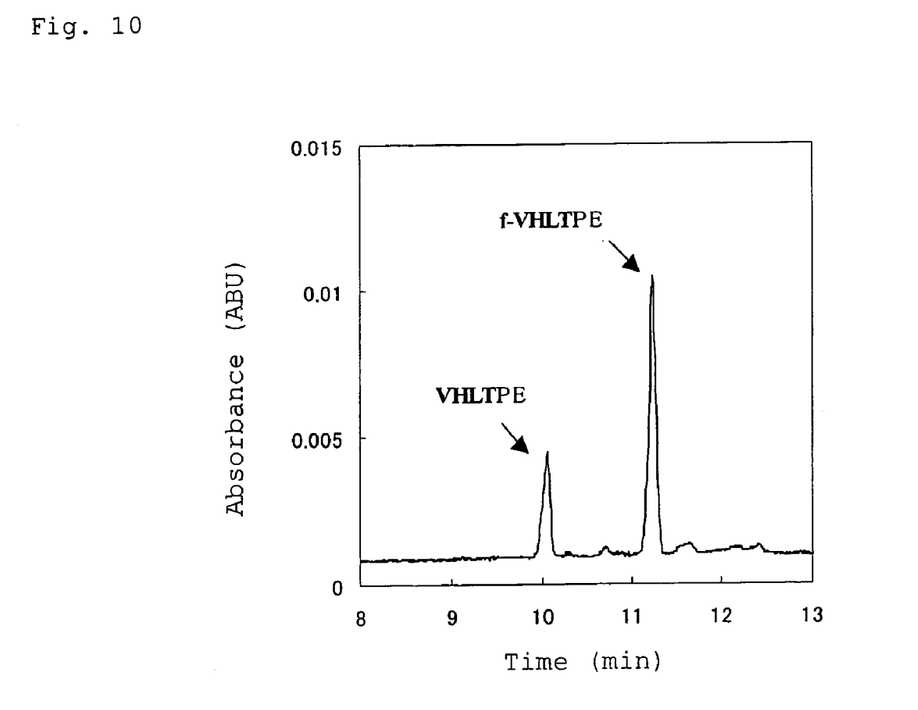
FIG. 10 shows the results of capillary electrophoresis obtained from the control solution 5 prepared by reacting purified water with fructosyl hexapeptide (f-VHLTPE; SEQ ID NO: 5).

FIG. 9 shows the results obtained from the reaction mixture 5, and FIG. 10 shows the results obtained from the control solution 5. Whereas FIG. 10 reveals a peak attributed to f-VHLTPE (area: 54 mABU×sec; SEQ ID NO: 5) and a peak attributed to VHLTPE (area: 21 mABU×sec; SEQ ID NO: 5), FIG. 9 reveals that the peak attributed to f-VHLTPE is lowered (area: 9 mABU×sec; SEQ ID NO: 5) and the peak attributed to VHLTPE is increased (area: 48 mABU×sec; SEQ ID NO: 5).

These results substantiate that use of the enzyme originating from a plant belonging to the family Rosaceae is effective for defructosylation of fructosyl peptides.

Example 5

Method of Defructosylating Fructosyl Peptide (Use of Defructosylation Enzyme Originating from a Plant belonging to the family Vitaceae)

The crude enzyme solution prepared in Example 2 was also tested under conditions similar to those of Example 4. However, as the N-terminal-valine fructosylated peptide, f-VH (SEQ ID NO: 1) containing no VH (SEQ ID NO: 1) was employed, and reaction was performed for 16 hours at 37° C. (reaction mixture 6). A control test was performed in a manner similar to that described in Example 4 (control solution 6).

Figure 11:
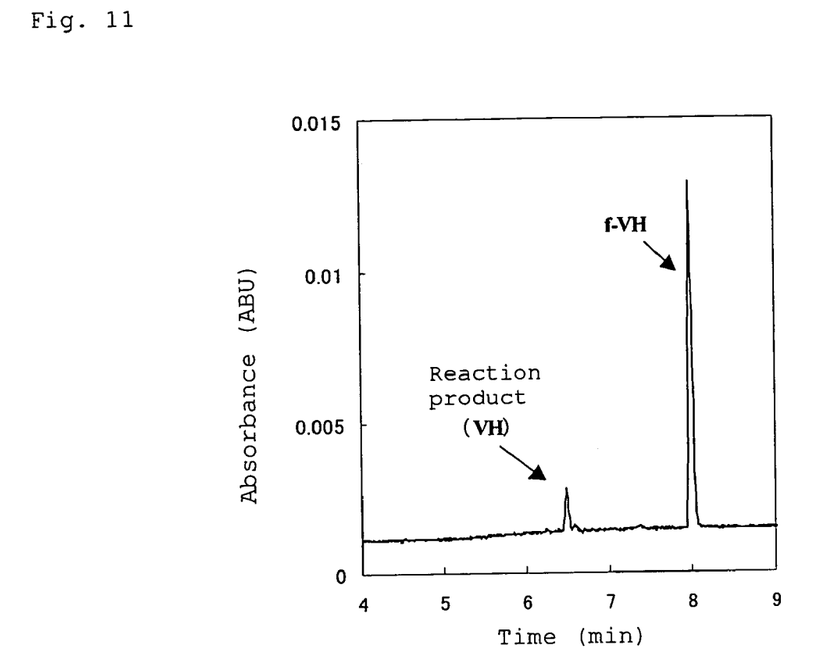
FIG. 11 shows the results of capillary electrophoresis obtained from the reaction mixture 6 prepared by reacting a Vitaceae-plant-origin defructosylation enzyme with fructosyl dipeptide (f-VH; SEQ ID NO: 1).
Figure 12:
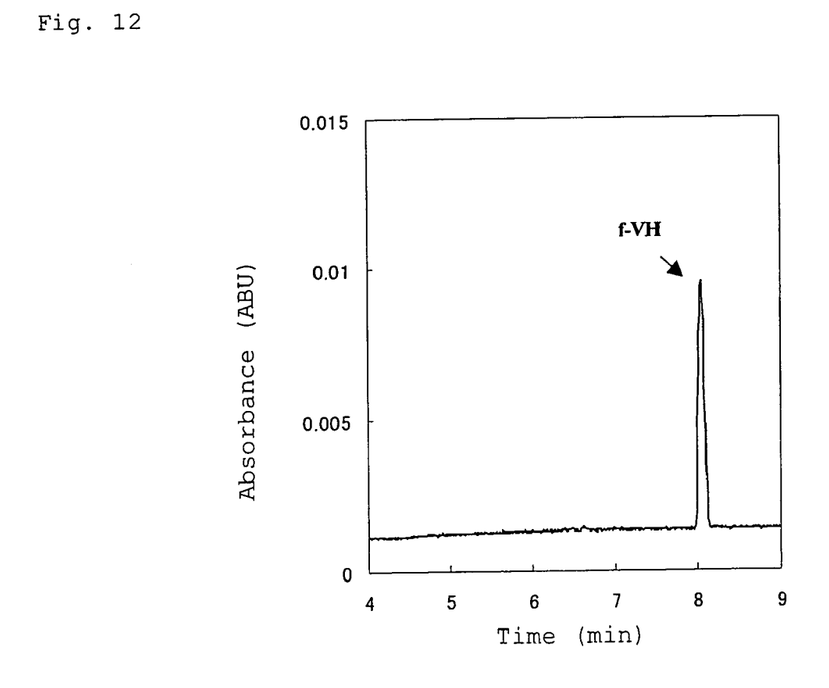
FIG. 12 shows the results of capillary electrophoresis obtained from the control solution 6 prepared by reacting purified water with fructosyl dipeptide (f-VH; SEQ ID NO: 1).

FIG. 11 shows the results obtained from the reaction mixture 6, and FIG. 12 shows the results obtained from the control solution 6. Whereas FIG. 12 reveals only a peak attributed to f-VH (area: 42 mABU×sec; SEQ ID NO: 1), FIG. 11 reveals a lowered peak attributed to f-VH (area: 36 mABU×sec: SEQ ID NO: 1) and a newly generated peak attributed to the reaction product (area: 4 mABU×sec). In order to identify the new peak, a small amount of VH (SEQ ID NO: 1) was added to the reaction mixture, followed by capillary electrophoresis. The peak attributed to the reaction product coincided with that of VH (SEQ ID NO: 1), thus confirming the reaction product to be VH (SEQ ID NO: 1).

These results substantiate that use of the enzyme originating from a plant belonging to the family Vitaceae is effective for defructosylation of fructosyl peptides.

Example 6

Method of Defructosylating Fructosyl Peptide (Use of Defructosylation Enzyme Originating from a Plant belonging to the family Umbelliferae)

The crude enzyme solution prepared in Example 3 was also tested under conditions similar to those of Example 5 (reaction mixture 7).

Figure 13:
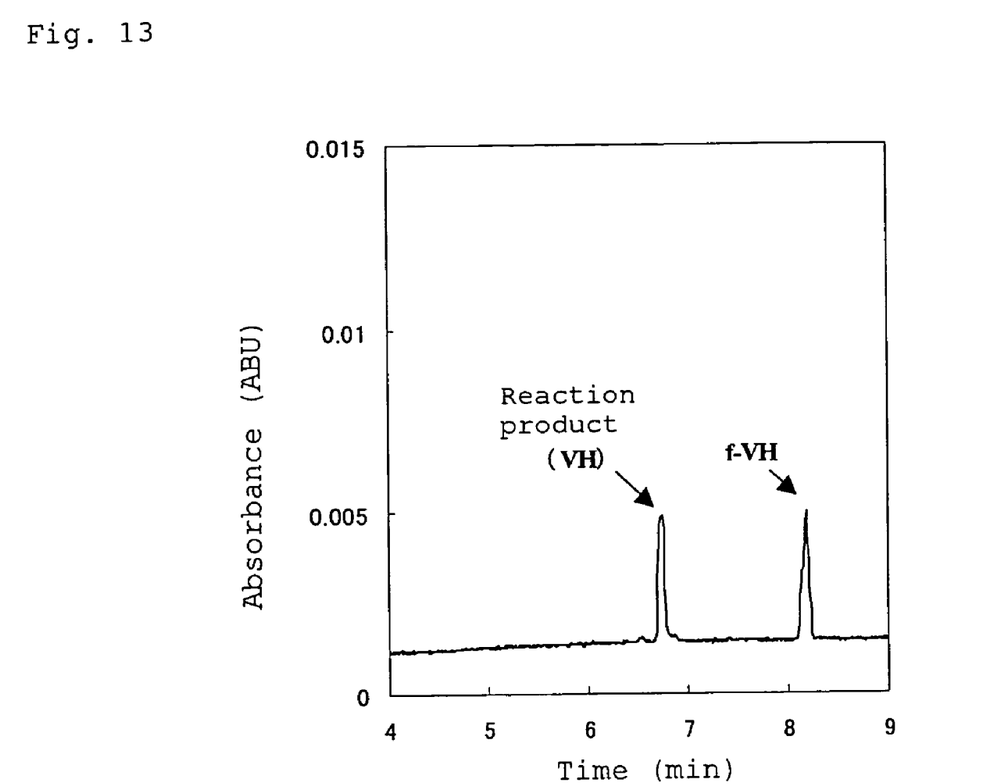
FIG. 13 shows the results of capillary electrophoresis obtained from the reaction mixture 7 prepared by reacting an Umbelliferae-plant-origin defructosylation enzyme with fructosyl dipeptide (f-VH; SEQ ID NO: 1).

FIG. 13 shows the results obtained from the reaction mixture 7. For the results from the control solution, FIG. 12 is again referred to. Whereas FIG. 12 reveals only a peak attributed to f-VH (area: 42 mABU×sec; SEQ ID NO: 1), FIG. 13 reveals a lowered peak attributed to f-VH (area: 16 mABU×sec; SEQ ID NO: 1) and a newly generated peak attributed to the reaction product (area: 16 mABU×sec). In order to identify the new peak, a small amount of VH (SEQ ID NO: 1) was added to the reaction mixture, followed by capillary electrophoresis. The peak attributed to the reaction product coincided with that of VH (SEQ ID NO: 1), thus confirming the reaction product to be VH (SEQ ID NO: 1).

These results substantiate that use of the enzyme originating from a plant belonging to the family Umbelliferae is effective for defructosylation of fructosyl peptides.

---

The invention claimed is:

1. A method for removing fructosyl group from an isolated fructosylated peptide or a fructosylated protein, comprising:
    reacting the fructosylated peptide or protein with a aqueous extract from *Pyrus pyrifolia, Vitis vinifera,* or *Daucus carota* containing an enzyme that removes a fructosyl group from a peptide or polypeptide without removing an amino acid residue of said peptide or polypeptide.

2. The method of claim 1, wherein said aqueous extract is from *Pyrus pyrifolia.*

3. The method of claim 1, wherein said aqueous extract is from *Vitis vinifera.*

4. The method of claim 1, wherein said aqueous extract is from *Daucus carota.*

5. The method of claim 1, wherein said enzyme removes an N-terminal fructosyl group from a fructosylated peptide or fructosylated protein comprising Val-His (SEQ ID NO: 1).

6. The method of claim 1, wherein said enzyme removes an N-terminal fructosyl group from a fructosylated peptide or fructosylated protein comprising Val-His-Leu (SEQ ID NO: 2).

7. The method of claim 1, wherein said enzyme removes an N-terminal fructosyl group from a fructosylated peptide or fructosylated protein comprising Val-His-Leu-Thr (SEQ ID NO: 3).

8. The method of claim 1, wherein said enzyme removes an N-terminal fructosyl group from a fructosylated peptide or fructosylated protein comprising Val-His-Leu-Thr-Pro (SEQ ID NO: 4).

9. The method of claim 1, wherein said enzyme removes an N-terminal fructosyl group from a fructosylated peptide or fructosylated protein comprising Val-His-Leu-Thr-Pro-Glu (SEQ ID NO: 5).

10. The method of claim 1, wherein the fructosylated protein is hemoglobin A1c.

11. The method of claim 1, further comprising detecting at least one reaction product of removal of a fructosyl group from said fructosylated peptide or fructosylated protein.

12. The method of claim 11, comprising detecting the reaction product hydrogen peroxide.

13. The method of claim 11, comprising detecting the reaction product glucosone.

14. The method of claim 11, comprising detecting the reaction product glucose.

15. The method of claim 11, comprising detecting the reaction product defructosyl peptide.

* * * * *

SEQUENCE LISTING

```
<160> NUMBER OF SEQ ID NOS: 5

<210> SEQ ID NO 1
<211> LENGTH: 2
<212> TYPE: PRT
<213> ORGANISM: Artificial Sequence
<220> FEATURE:
<223> OTHER INFORMATION: Synthetic Peptide

<400> SEQUENCE: 1

Val His
1

<210> SEQ ID NO 2
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 2

Val His Leu
1

<210> SEQ ID NO 3
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 3

Val His Leu Thr
1

<210> SEQ ID NO 4
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 4

Val His Leu Thr Pro
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic Peptide
```

```
<400> SEQUENCE: 5

Val His Leu Thr Pro Glu
1               5
```